(12) United States Patent
Minamitani

(10) Patent No.: US 9,568,455 B2
(45) Date of Patent: Feb. 14, 2017

(54) CORROSIVE ENVIRONMENT MONITORING APPARATUS AND METHOD

(75) Inventor: Rintaro Minamitani, Tokyo (JP)

(73) Assignee: HITACHI, LTD., Tokyo (JP)

( * ) Notice: Subject to any disclaimer, the term of this patent is extended or adjusted under 35 U.S.C. 154(b) by 339 days.

(21) Appl. No.: 14/239,851

(22) PCT Filed: Sep. 20, 2011

(86) PCT No.: PCT/JP2011/071314
§ 371 (c)(1),
(2), (4) Date: Feb. 20, 2014

(87) PCT Pub. No.: WO2013/042179
PCT Pub. Date: Mar. 28, 2013

(65) Prior Publication Data
US 2014/0190239 A1    Jul. 10, 2014

(51) Int. Cl.
*G01N 17/02* (2006.01)
*G01N 33/00* (2006.01)
*G01N 17/04* (2006.01)
*G01N 17/00* (2006.01)

(52) U.S. Cl.
CPC ........ *G01N 33/0004* (2013.01); *G01N 17/002* (2013.01); *G01N 17/006* (2013.01); *G01N 17/043* (2013.01); *G01N 17/046* (2013.01)

(58) Field of Classification Search
CPC .... G01N 17/006; G01N 17/04; G01N 17/043; G01N 17/046
See application file for complete search history.

(56) References Cited

U.S. PATENT DOCUMENTS

| | | | |
|---|---|---|---|
| 5,411,890 A | 5/1995 | Falat | |
| 6,361,963 B1 | 3/2002 | Smith et al. | |
| 2010/0011886 A1* | 1/2010 | Czapiewski | G01M 15/14 73/863.23 |

FOREIGN PATENT DOCUMENTS

| | | |
|---|---|---|
| JP | 6-117976 A | 4/1994 |
| JP | 7-146285 A | 6/1995 |
| JP | 2003-294606 A | 10/2003 |
| JP | 2005-121510 A | 5/2005 |
| JP | 2008-281499 A | 11/2008 |
| JP | 2009-145146 A | 7/2009 |

* cited by examiner

Primary Examiner — Paul West
(74) Attorney, Agent, or Firm — Baker Botts L.L.P.

(57) ABSTRACT

An object of the present invention is to provide a corrosive environment monitoring apparatus and a corrosive environment monitoring method for evaluating the corrosiveness of an ambient environment simply and accurately in a short time period.

The corrosive environment monitoring apparatus (1) of this invention has at least one vent duct (3a, 3b, 3c) in which specimens (2a, 2b, 2c) are installed so that the corrosiveness of the ambient environment is measured from the corroded conditions of the specimens (2a, 2b, 2c). The regions of the specimens (2a, 2b, 2c) in one vent duct (3a, 3b, 3c), which are subject to measurement, are made of the same metallic material. If a plurality of vent ducts (3a, 3b, 3c) are provided, these vent ducts (3a, 3b, 3c) are arranged in parallel with one another.

16 Claims, 12 Drawing Sheets

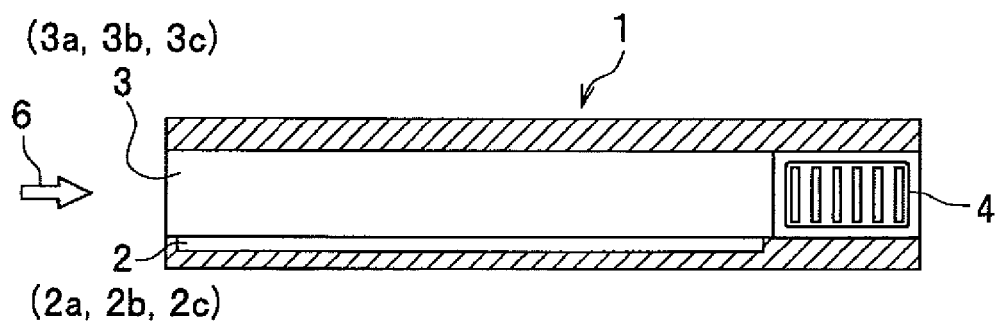
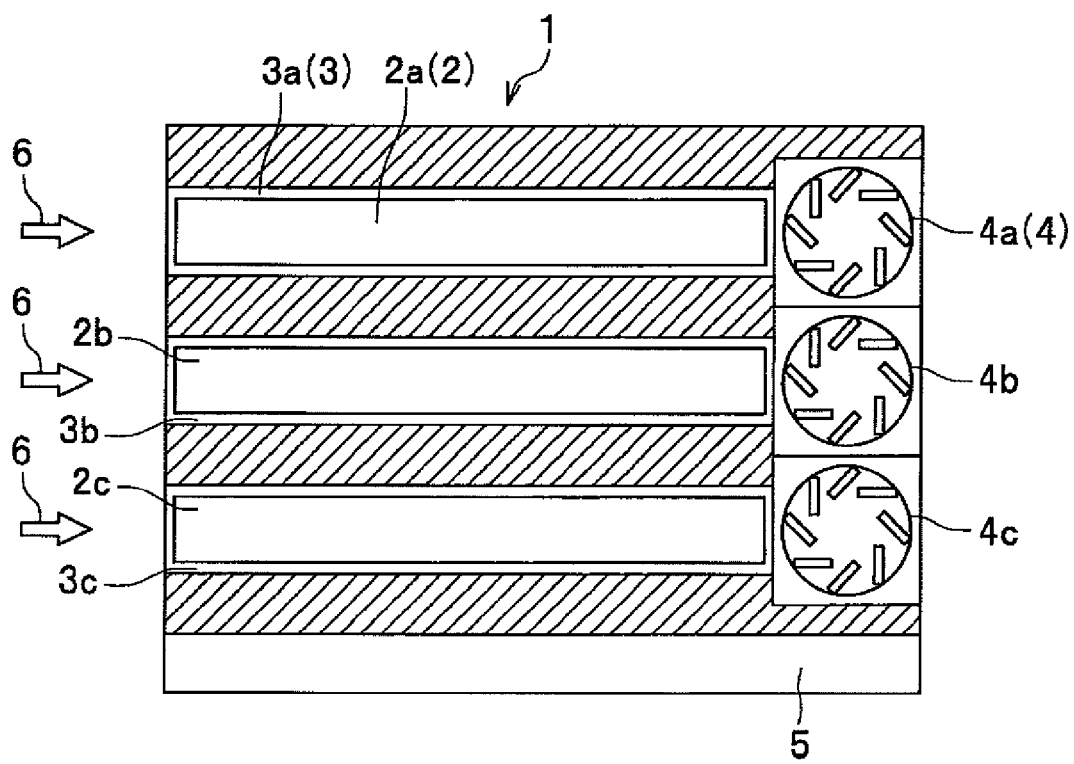

F I G . 5
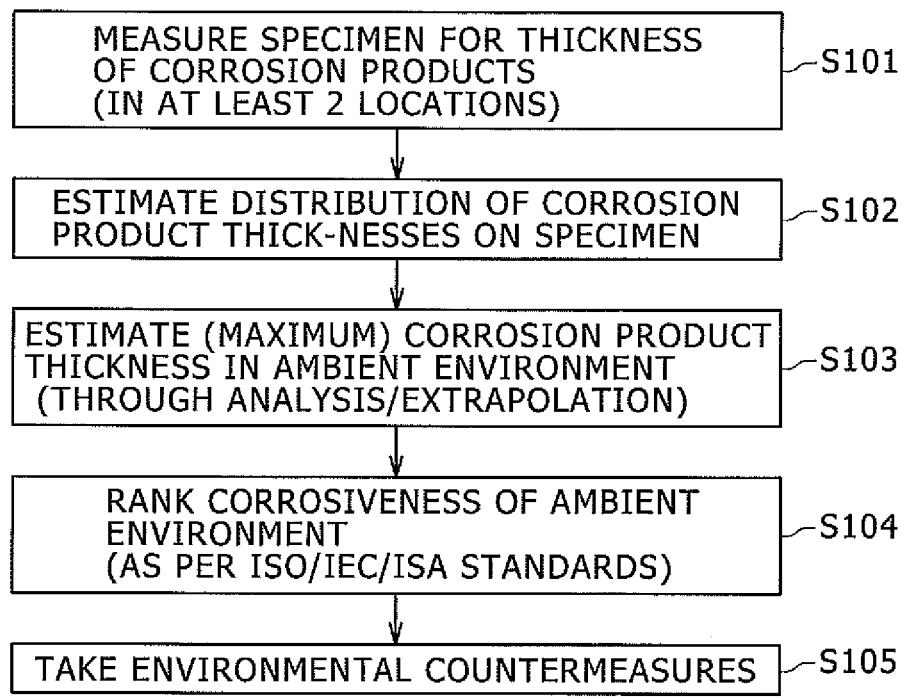

Prior Art

CORROSIVE ENVIRONMENT MONITORING APPARATUS AND METHOD

TECHNICAL FIELD

The present invention relates to a corrosive environment monitoring apparatus and a corrosive environment monitoring method for measuring the degree of corrosion of electrical and electronic equipment attributable to corrosive gases or the like that may exist in the indoor environment.

BACKGROUND ART

As prior (background) art of this technical field, there exits Patent Literature 1 cited below.

Patent Literature 1 includes the following description: "After metals, ceramics, or metal salts are left for a predetermined time period in the environmental atmosphere as the measuring object, gas components that have been adsorbed thereby are analyzed. In particular, porous metals or ceramics (transition metal oxides) have a high selective absorptivity for NOx; porous ceramics (rare-earth element oxides) have a high selective absorptivity for $CO_2$; and specific chlorides such as copper chloride and silver chlorides have a high selective absorptivity for $SO_2$." Patent Literature 1 also includes descriptions of a testing kit that houses specimens of these materials in a case; and a testing kit protective case, umbrellas, and a forced air feeder for commercializing the testing kit.

FIGS. 11A and 11B show a typical prior art environment monitoring apparatus. FIGS. 11A and 11B are a side view and a top view, respectively, showing the internal structure of a protective case for the prior art environment monitoring apparatus.

In the prior art environment monitoring apparatus 100, a vent duct 112r of the protective case 112 houses specimens 111 of copper (111a), silver (111b), aluminum (111c), iron (111d), and an iron nickel alloy (111e), for example.

When a corrosive gas 106 that is present in the ambient environment is allowed to flow in the direction indicated by a white arrow, corrosive substances contained in the corrosive gas 106 adhere to the surfaces of the specimens 111 and discolor them. If the protective case 112 is made of a transparent material, the discoloration of the specimens 111 can be visually inspected (seen through) from outside of the protective case 112.

The specimens 111 collected after exposure to the corrosive gas 106 for the predetermined time period are measured for the degree of corrosion over predetermined regions by gravimetric method, by quantitative analysis for corrosive gas elements using fluorescent X-rays, and by film thickness measuring through constant-current electrolysis.

For example, Patent Literature 1 reports that the corrosive gas concentration in the environment as the measuring object can be estimated from the results of the quantitative analysis of corrosive gas elements in corrosion products formed on the surfaces of the metal specimens 111 due to the presence of the corrosive gas 106. It is also reported that the corrosiveness of the environment of interest is categorized depending on the thickness of the corrosion product on a copper plate exposed for one month to the environment as the measuring object in accordance with the IEC654-4 standard, ISO11844-1 standard, ISO9223 standard, and ISA71.04 standard.

Specifically, the specimens 111 exposed for the predetermined time period to the atmosphere as the measuring object are analyzed by fluorescent X-ray analysis and X-ray luminous energy analysis for corrosive gas components (sulfur in sulfur oxides and sulfides, nitrogen in nitrogen oxides, and chorine in chlorides) in the corrosion products formed on the surfaces of the specimens 111. Also, the corrosive gas composition is analyzed by color specification data analysis in terms of brightness, hue, and saturation of the corrosion products.

Furthermore, Patent Literature 1 discloses a method which, where it is desired to shorten the time of exposure to the atmosphere of the ambient environment, involves forcibly feeding the corrosive gas of the ambient atmosphere to the specimens 111 to promote the corrosion reaction thereof (see paragraph 0050, FIG. 8, of Patent Literature 1).

In the prior art environment monitoring apparatus 100, the corrosive gas 106 in the ambient environment is allowed to flow toward or diffuse around the specimens 111 via an opening 112k of the protective case 112, with or without fans.

PRIOR ART LITERATURE

Patent Literature

[Patent Literature 1]
JP-6-117976-A (paragraph 0050, FIG. 8, etc.)

SUMMARY OF THE INVENTION

Problems to be Solved by the Invention

Meanwhile, electrical and electronic equipment is required to stay reliable for extended periods of time for the purpose of stably operating the target device to be controlled.

Also, the high-density mounting structure has been adopted to speed control operations and to save occupying volumes, with numerous electrical and electronic components of the micro wiring structure and thin film plating structure mounted on electrical and electronic equipment. Since even limited corrosion damage of these electrical and electronic components can change their electrical or magnetic characteristics leading to failures or malfunctions, how to suppress such corrosion damage is one of the challenges to be dealt with in maintaining the reliability of electrical and electronic equipment.

Thus there has been a need for evaluating, simply and accurately over a short time period, the corrosiveness of the environment in which electrical and electronic equipment is installed so that the corrosion prevention measures suitable for the degree of corrosiveness of the environment may be reflected in the design and maintenance of such equipment.

The technique described in Patent Literature 1 of the prior art has the problem about underestimating the degree of corrosion on the metal specimens exposed to the installation environment as the measuring object for the predetermined time period.

According to Patent Literature 1 of the prior art, as shown in FIGS. 11A and 11B, a plurality of specimens 111 are set up inside a single protective case 112 and are exposed for the predetermined time period to the atmospheric environment (installation environment) as the measuring object. The specimens 111 are then inspected for corroded conditions, whereby the effects of various corrosive gases are evaluated at one time.

The IEC, ISO, and ISA standards stipulate such metallic materials as copper, silver, aluminum, iron, and zinc for use as the specimens 111 to be evaluated for corrosion in the atmospheric environment (installation environment) as the measuring object. Copper, silver, aluminum, iron, and zinc are each known to be corroded to different degrees of severity by one of the corrosive gases of $SO_2$, $NO_2$, and $H_2S$.

In the environment monitoring apparatus 100 of the prior art, the corrosive gas 106 contained in the atmosphere as the measuring object is allowed to flow toward or diffuse around the reed-shaped specimens 111 via the opening 112k of the protective case 112. Here, the individual specimens 111 are set up serially in the flowing or diffusing direction of the corrosive gas 106, so that the corrosive gas 106 is consumed by the upstream-side specimens 111 (on the side of the specimen 111a) close to the opening 112k.

For this reason, the corrosive gas 106 reaching the downstream-side specimens 111 (on the side of the specimen 111e) away from the opening 112k is lower in concentration than the corrosive gas 106 in the ambient atmosphere. That is, where each of the specimens 111 is considered individually, the same specimen is corroded more severely on its upstream edge than on its downstream edge.

Depending on the surface location of the specimens 111 in the protective case 112, the corrosion products caused by the corrosive gas 106 are estimated to vary in thickness by tens of percents. It follows that the way the specimens 111 are arrayed inside the protective case 112 is estimated to vary their degrees of corrosion.

Below are some results of having qualitatively examined how the specimens arrayed serially in the flowing direction of the corrosive gas 106 were affected thereby.

Of the materials of copper, silver, aluminum, iron, and iron nickel alloy used as the specimens 111, silver may be selected for explanation hereunder.

Explained here are five silver specimens 111 (each specimen is 5 mm long crosswise as viewed in FIG. 11B) arrayed 3 mm apart (see FIG. 11B), the thicknesses of their corrosive substances being normalized with regard to the thickness of the corrosion products on the upstream edge of each specimen 111 (the thickness of the corrosion products on the upstream edge of the specimens 111 is taken as 1).

FIG. 12 shows a typical result of analysis by the prior art environment monitoring apparatus using a convective diffusion equation (1), to be discussed later, i.e., the result of having normalized the thicknesses of corrosion products with regard to the thickness of the corrosion products on the upstream edge of the specimens (the thickness of the corrosion products on the upstream edge of the specimens 111 is taken as 1). The horizontal axis of FIG. 12 denotes distances s1 (see the upper subfigure in FIG. 13) from the most upstream edge of the specimens 111.

It is assumed that H=10 mm, where H stands for the height of the vent duct 112r from the measuring plane of the specimens 111, and that Vd=0.01 mm/s (Vd is the deposition rate of corrosive substances (corrosion products) onto the measuring plane of the specimens 111).

The relations shown in FIG. 12 were obtained using the equation (1) to be discussed later. On average, the thickness of the corrosion products on the downstream edge (point b in FIG. 12) of the silver specimens 111 was found reduced to about 60% of the thickness on the upstream edge (point a in FIG. 12).

That is, there is a tendency for the corrosion products of the specimens 111 to be thicker on their upstream edge and to be thinner the further on the downstream side.

Thus the prior art environment monitoring apparatus 100 tends to underestimate the corrosive substances in the ambient environment as the measuring object the further on the downstream side in the vent duct 112r (toward the specimen 111e in FIG. 11B).

FIG. 13 shows typical measurements taken by the prior art environment monitoring apparatus of the degrees of corrosion on the specimens when they are exposed for the predetermined time period to the ambient (installation) environment as the measuring object.

The upper subfigure in FIG. 13 shows the specimens 111a through 111e viewed from above as they are arrayed serially in the vent duct 112r (see FIG. 11B). The lower subfigure shows the thicknesses of the corrosion products on the specimens 111a through 111e. The horizontal axis of the lower subfigure in FIG. 13 denotes the distances s1 from the upstream edge of the specimen 111a, and the vertical axis of the lower subfigure in FIG. 13 represents the thicknesses of the corrosion products on the specimens 111a through 111e.

It is evident that the farther from the opening 112k of the protective case 112 (i.e., the farther away from the specimen 111a toward the specimen 111e), the smaller the thickness of the corrosion products.

As explained above, when the corrosion products in downstream regions, where they are relatively thin, are analyzed for thickness, i.e., where the specimens 111 are located away from the opening 112k, e.g., specimen 111e in FIGS. 11A and 11B, the degree of corrosion on the specimens 111 is found declined, and the thickness of the corrosion products on the specimens 111 is evaluated to be smaller than under the proper conditions of environmental corrosiveness. This is the first problem (task).

Also, when a single specimen 111 is considered in prior art, both edges of the specimen 111 tend to be more corroded, and the further toward the middle of the specimen, the smaller the degree of corrosion tends to become. Thus if relatively smaller regions close to the middle of the specimen are analyzed for the degree of corrosion, the degree of corrosion of the specimen tends to be underestimated. This is the second problem (task).

In addition, the degree of corrosion of the specimens 111 is analyzed by gravimetric method, by quantitative analysis for corrosive gas elements using fluorescent X-rays, and by film thickness measuring through constant-current electrolysis. These evaluations deal with the mean values of all specimens 111 or the values of locations close to the middle of each specimen where the degree of corrosion tends to be smaller. This leads to underestimating the degree of corrosion of the specimens 111, which constitutes the third problem (task).

In view of the above circumstances, an object of the present invention is to provide a corrosive environment monitoring apparatus and a corrosive environment monitoring method for evaluating the corrosiveness of an ambient environment simply and accurately in a short time period.

Means for Solving the Problem

A corrosive environment monitoring apparatus described in claim 1 of this invention has at least one vent duct in which a specimen is installed, the corrosive environment monitoring apparatus adapted to measure the corrosiveness in an ambient environment from the corroded condition of the specimen, wherein the specimen has a region subject to the measurement formed in the vent duct, the region being made of the same metallic material, and wherein, if a plurality of vent ducts are provided, the vent ducts are arranged in parallel with one another.

A corrosive environment monitoring apparatus described in claim 2 of this invention has one or more vent ducts in which specimens are installed, the corrosive environment monitoring apparatus adapted to measure the corrosiveness in an ambient environment from the corroded condition of the specimens, wherein the specimens each have a region subject to the measurement, the region being elongated in shape and being made of the same metallic material, and wherein the longitudinal direction of each of the regions subject to the specimen measurement formed in the vent ducts is in parallel with or along the direction in which a corrosive substance in the ambient environment passing through the vent ducts flows.

A corrosive environment monitoring method described in claim 9 of this invention is one in which at least one vent duct having a specimen installed thereon is provided and the corrosiveness in an ambient environment is measured from the corroded condition of the specimen, wherein monitoring is performed by installing the specimen having a region subject to the measurement formed in one vent duct or a plurality of vent ducts arranged in parallel with one another, the region being made of the same metallic material.

A corrosive environment monitoring method described in claim 10 of this invention is one in which one or more vent ducts each having a specimen installed thereon are provided and the corrosiveness in an ambient environment is measured from the corroded condition of the specimens, wherein the specimens each have a region subject to the measurement formed in the vent duct, the region being elongated in shape and being made of the same metallic material, and wherein monitoring is performed by installing the specimens in such a manner that the longitudinal direction of each of the regions subject to the measurement is in parallel with or along the direction in which a corrosive substance in the ambient environment passing through the vent ducts flows.

Effect of the Invention

According to the present invention, it is possible to evaluate the corrosiveness of the ambient environment of electrical and electronic equipment or the like simply and accurately in a short time period.

BRIEF DESCRIPTION OF THE DRAWINGS

FIG. 2A is a side view showing an internal structure of the corrosive environment monitoring apparatus as the embodiment.

FIG. 2B is a top view showing the internal structure of the corrosive environment monitoring apparatus as the embodiment.

FIG. 5 is a chart showing the steps in which the corrosive environment monitoring apparatus evaluates the corrosiveness of the atmosphere in the ambient environment as the measuring object.

MODE FOR CARRYING OUT THE INVENTION

Figure 1:
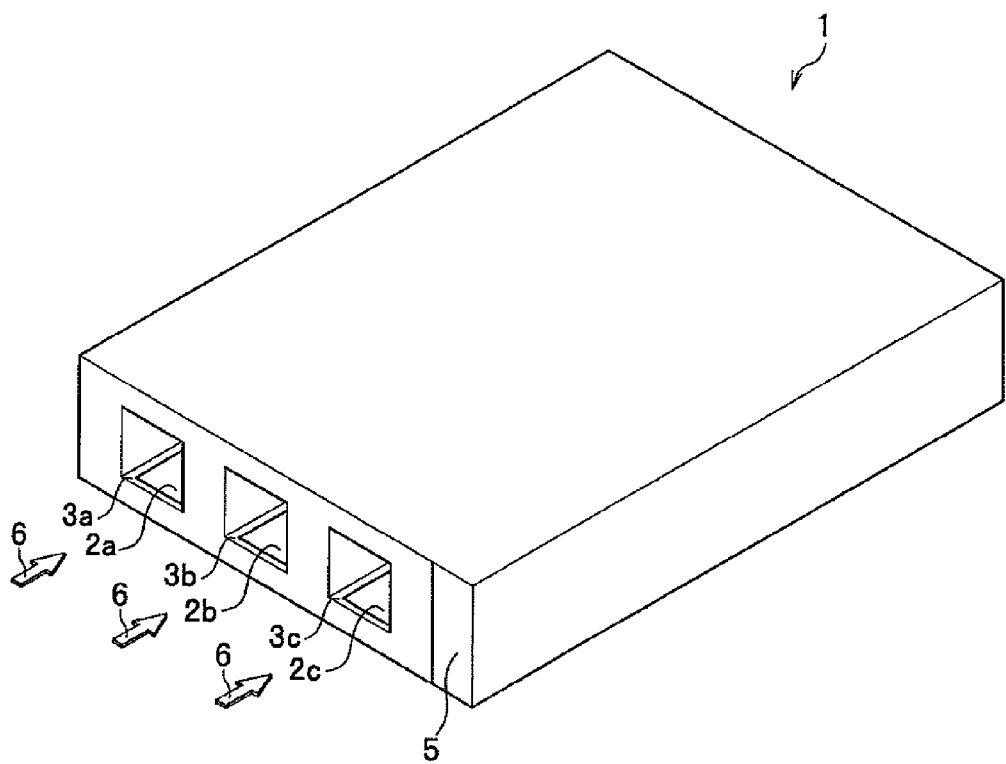
FIG. 1 is a perspective view showing an external appearance of a corrosive environment monitoring apparatus as an embodiment of the present invention.

Some embodiments of the present invention are explained below in reference to the accompanying drawings. FIG. 1 is a perspective view showing an external appearance of a corrosive environment monitoring apparatus as one embodiment of the present invention. FIG. 2A is a side view showing an internal structure of the corrosive environment monitoring apparatus as the embodiment. FIG. 2B is a top view showing the internal structure of the corrosive environment monitoring apparatus as the embodiment.

As some embodiments, there will be explained below a corrosive environment monitoring apparatus 1 and a method for use therewith for measuring (estimating) the degree of corrosion on electrical and electronic equipment (not shown) caused by a corrosive gas found primarily in the atmosphere of the environment in which the electrical and electronic equipment is installed. For example, the electrical and electronic equipment may be precision instruments and computers for controlling machines.

In the corrosive environment monitoring apparatus 1, there are provided three vent ducts 3 (3a, 3b, 3c) which have a rectangular cross section each and which extend longitudinally throughout the apparatus to form a ventilation space therein. Downstream of the vent ducts 3 (3a, 3b, 3c), fans 4 (4a, 4b, 4c) are provided to promote the ventilation flow in the vent ducts 3. The fans 4 (4a, 4b, 4c) are driven with a voltage coming from a power source 5 (see FIGS. 2A and 2B).

Rectangular plate-like specimens 2 (2a, 2b, 2c) are installed in the vent ducts 3 (3a, 3b, 3c), respectively, of the corrosive environment monitoring apparatus 1 in such a manner that the longitudinal direction of the specimens is parallel to the longitudinal direction of the vent ducts 3. Each of the specimens 2 (2a, 2b, 2c) is made of one metallic material that differs from one specimen to another.

The corrosiveness of the ambient environment (installation environment) as the measuring object is evaluated by first measuring the degree of corrosion (thickness of corrosion products) on the surfaces of the specimens 2 (2a, 2b, 2c) along the direction in which corrosive substances 6 contained in the atmosphere of the ambient environment passing through the vent ducts 3 (3a, 3b, 3c) flow or diffuse, and by estimating the distribution of the thicknesses of corrosion products on the specimen surfaces.

The corrosive substances 6 include corrosive gases, airborne sea salt and dust, to name a few. In the ensuing description, the corrosive gas will be used as the representative example of the corrosive substances 6.

<Specimens 2>

The specimens 2 should preferably have the shape of an elongated rectangular thin reed each so that the distribution of the thicknesses of the corrosion products formed on the specimen surfaces may be measured accurately. Also, the specimens 2 should preferably be installed in the corrosive environment monitoring apparatus 1 in such a manner that the longitudinal direction of each specimen 2 made of the same metallic material in each vent duct 3 is parallel to or along the direction in which the corrosive gas in the ambient environment flows or diffuses inside the vent ducts 3.

The aspect ratio of the reed-shaped specimen 2 may be of any value as long as the specimen permits measurement of how the thicknesses of corrosion products are distributed with regard to the flowing or diffusing direction of ventilation.

FIGS. 2A and 2B show that the specimens 2a, 2b and 2c, typically made of copper, silver and gold plating (on the copper bed) respectively, are housed in the vent ducts 3 (3a, 3b, 3c).

Copper, silver, and gold plating (on the copper bed) are frequently utilized as the materials (base metals) of electrical and electronic components. Furthermore, these materials are used in surveying the installation environment of electrical and electronic equipment. Also usable as the materials for the specimens 2 are iron, iron nickel alloys, aluminum, and zinc which are employed in environmental surveys of the outdoor atmosphere. Thus pure metals and alloys other than copper and silver may also be used as the specimens 2.

In each vent duct 3, the specimen 2 made of one type of metal (including an alloy) is installed.

If a plurality of specimens 2 (2a, 2b, 2c) are exposed to the atmosphere as shown in FIG. 2B, a plurality of vent ducts 3 (3a, 3b, 3c) are provided, and each specimen 2 made of one type of metal is installed in each vent duct 3.

Figure 3A:
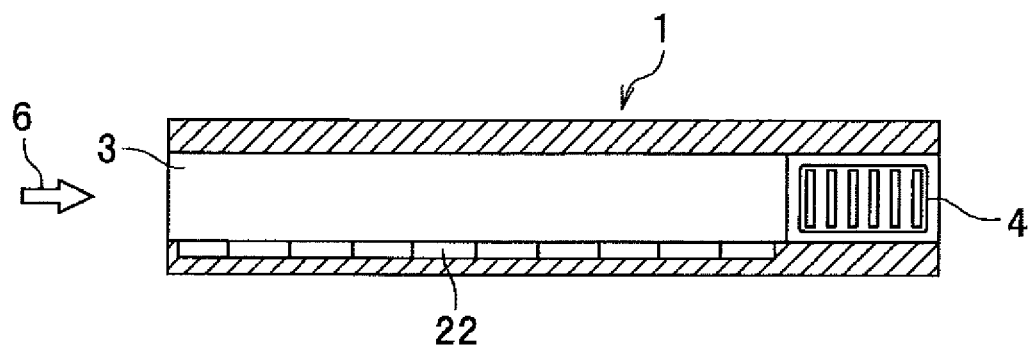
FIG. 3A is a side view showing an internal structure of the corrosive environment monitoring apparatus as the embodiment in which small-piece specimens are used.
Figure 3B:
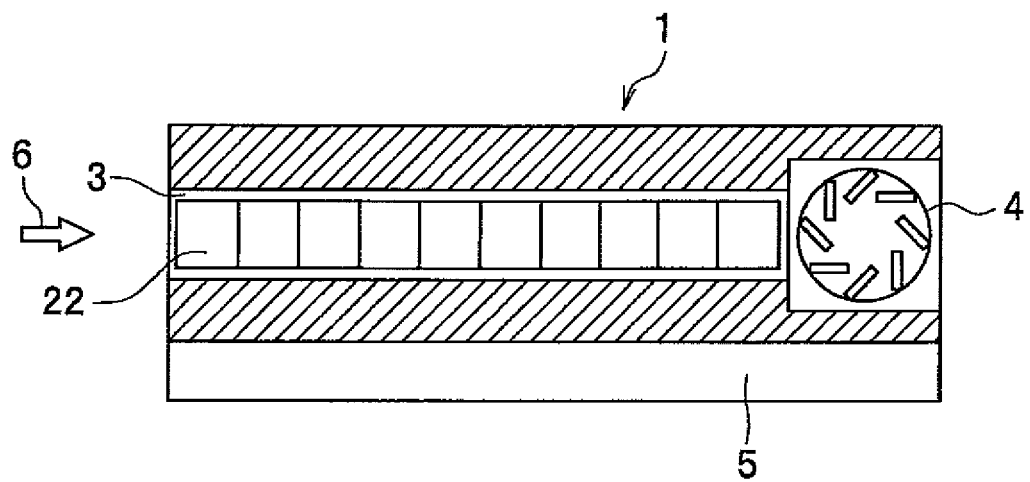
FIG. 3B is a top view showing the internal structure of the corrosive environment monitoring apparatus as the embodiment in which small-piece specimens are used.

As long as they are made of one type of metal, small-piece specimens 22, which are cut into small pieces, may be used as indicated in FIGS. 3A and 3B.

In view of corrosion thickness measurement, to be discussed later, the adjacent small-piece specimens 22 should preferably be arrayed with no gap therebetween so as to suppress ventilation turbulence between specimens, which will affect the deposition of corrosion products on the surfaces of the small-piece specimens 22.

The cross section of the vent ducts 3 may be of any shape: rectangular, circular, or polygonal. In view of the difficulty in manufacturing the corrosive environment monitoring apparatus 1 and the ease of measuring the degree of corrosion, to be discussed later, the vent ducts 3 should preferably have a simply structured rectangular cross section.

<Fans 4>

Inside the vent ducts 3, there are provided the fans 4 as the means for feeding the corrosive gas in the ambient environment toward the specimens 2 (2a, 2b, 2c) or 22 in the vent ducts. The fans 4 forcibly cause the air in the installation (ambient) environment to flow through the vent ducts 3, and the air is discharged from the corrosive environment monitoring apparatus 1 by way of the fans 4.

The fans 4 may be installed either upstream or downstream of the vent ducts 3 in which the specimens 2 or 22 are installed. However, the following points should be noted:

If installed upstream of the specimens 2 or 22, the fans 4 may disturb the flow of the corrosive gas toward the specimens 2 or 22. The corrosive substance 6 may also adhere to the fans 4. For these reasons, the fans 4 should preferably be set up downstream of the specimens 2 or 22.

Also, with the fans 4 stopped, the corrosive gas may be admitted into the vent ducts 3 by diffusion, not by the current of air caused by the fans 4.

When the corrosive gas present in the ambient environment as the measuring (monitoring) object is forcibly admitted into the vent ducts 3 inside the corrosive environment monitoring apparatus 1, the corrosion of the specimens 2 or 22 is promoted. Thus the forced admission of the corrosive gas is an effective means for improving the accuracy of measuring the thickness of the corrosion products formed by the corrosive gas.

Irregularities in the distribution of flow rates and their chronological changes inside the vent ducts 3 lead to an error in measuring the corrosion rate of the specimens 2. Thus in order to measure the corrosiveness of the environment accurately in a short time period, it is preferable to select the types of fans 4 that will reduce deviations in the distribution of flow rates and their chronological changes inside the vent ducts 3.

<Locations of the Specimens 2 Inside the Vent Ducts 3>

Figure 4A:
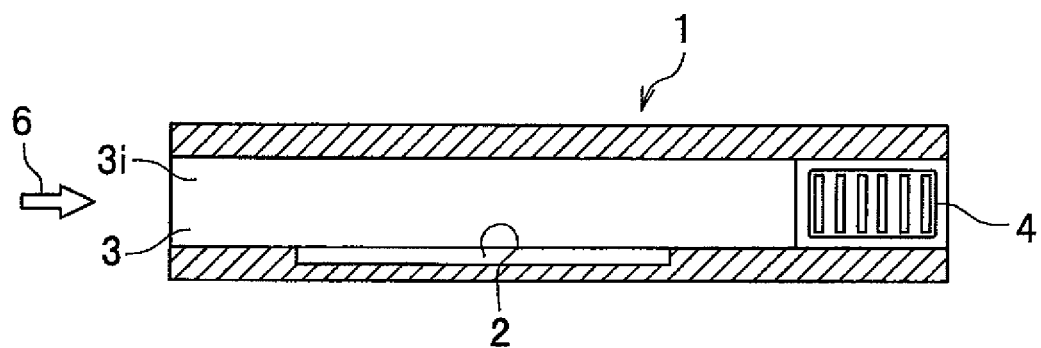
FIG. 4A is a side view showing an internal structure in which a specimen is located away from the inlet port of a vent duct of the corrosive environment monitoring apparatus.
Figure 4B:
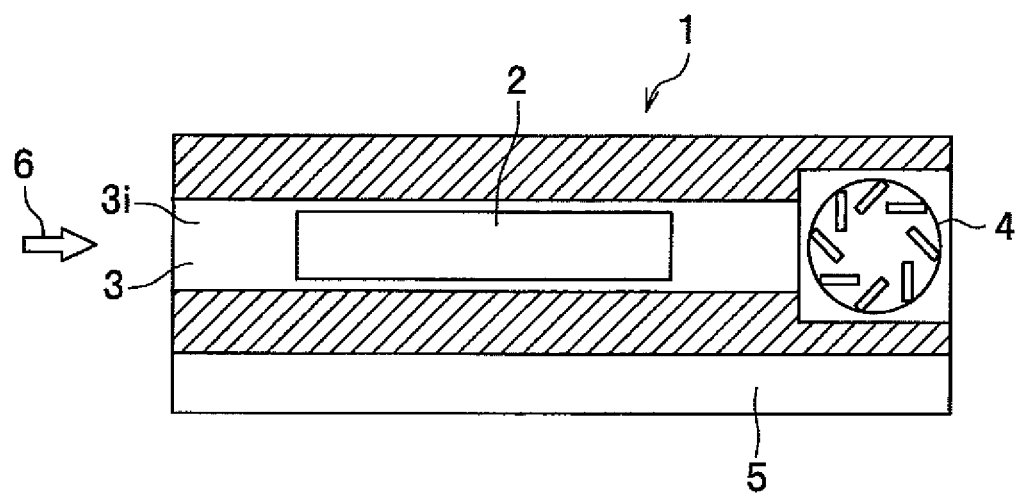
FIG. 4B is a top view showing the internal structure in which the specimen is located away from the inlet port of the vent duct of the corrosive environment monitoring apparatus.

FIG. 4A is a side view showing an internal structure in which a specimen is located away from the inlet port of a vent duct of the corrosive environment monitoring apparatus. FIG. 4B is a top view showing the internal structure in which the specimen is located away from the inlet port of the vent duct of the corrosive environment monitoring apparatus.

As shown in FIGS. 4A and 4B, the specimen 2 should preferably be located away from an inlet port (entrance) 31 so as to suppress the irregularities in the distribution of flow rates inside the vent duct 3.

In the environment monitoring apparatus 1, the reed-shaped specimen 2 is installed in such a manner that its upstream edge is positioned downstream of the location where the turbulence of the air flow disappears on the upstream side (near the inlet port 3i) of the vent duct 3 in the environment monitoring apparatus 1. This permits stable deposition of corrosion products on the surface of the specimen 2.

<Evaluation of the Corrosiveness of the Atmosphere in the Installation (Ambient) Environment>

Described below is the method for evaluating the corrosiveness of the atmosphere in the installation (ambient) environment as the measuring object.

FIG. 5 shows the steps of the method for evaluating the corrosiveness of the atmosphere in the installation (ambient) environment as the measuring object.

When the corrosive gas is consumed on the upstream side of one specimen 2, the volume of the corrosive gas is reduced by the amount consumed. It follows that the concentration of the corrosive gas reaching the downstream side of the specimen 2 becomes lower than in the ambient environment as the measuring object.

Therefore in prior art, as discussed above, there is a concern that those in-plane variations in the thickness of corrosion products which are dependent on the measuring location of the specimen can reduce the accuracy in evaluating the corrosiveness of the installation environment. Conversely, if the in-plane variations in the corrosion thickness of the specimen are utilized, the corrosiveness of the ambient environment can be accurately evaluated.

First, the corrosive environment monitoring apparatus 1 exposes the specimen 2 to the atmosphere for a predetermined time period before having the specimen 2 collected and measured for the thickness of corrosion products in at least two locations thereon along the flowing or diffusing direction (S101 in FIG. 5).

The measured values are used in analyses based on a convective diffusion equation, to be discussed later, for obtaining the distribution of deposition rates (rates at which corrosion products are formed by corrosion reaction) of the corrosive substance 6 contained in the corrosive gas in locations on the specimen 2 along the direction in which the corrosive gas flows or diffuses. The deposition rates and a testing (measuring) time are then used to acquire the thicknesses of the corrosion products (corrosion thickness distribution) on the specimen 2 (S102).

From the analysis data about the corrosion thickness distribution and from the measured corrosion thicknesses in at least two locations on the specimen 2 along the direction in which the corrosive gas flows or diffuses, the thickness of the corrosion products formed on the upstream edge of the specimen 2 (maximum thickness of the corrosion products formed on the specimen 2 exposed to the ambient environment as the measuring object) is estimated in reverse.

From the measured thicknesses of the corrosion products in at least two locations on the specimen 2 in the flowing or diffusing direction, the thickness of the corrosion products on the upstream edge of the specimen 2 may be simply extrapolated (S103). Incidentally, as with prior art, the degree of corrosion of the specimen 2 is measured by gravimetric method, by quantitative analysis for corrosive gas elements using fluorescent X-rays, and by film thickness measuring through constant-current electrolysis, for example. Alternatively, corrosion sensors using changes in electrical resistance or corrosion sensors based on a quartz crystal microbalance may be utilized.

Thus obtained, the thickness of the corrosion products on the edge (closest to the ambient environment) of the specimen 2 is evaluated in accordance with the IEC654-4, ISO11844-1, ISO9223, and ISA71.04 standards, whereby the corrosiveness of the ambient environment is categorized (ranked) (S104).

In this manner, the corrosiveness of the ambient environment for electrical and electronic equipment can be categorized simply and accurately in a short time period. Therefore, corrosion prevention measures corresponding to the categorized degree of corrosiveness of the environment in question can then be reflected in the design and maintenance of the equipment (S105).

<Measurement of the Degree of Corrosion on the Specimen 2>

Figure 6:
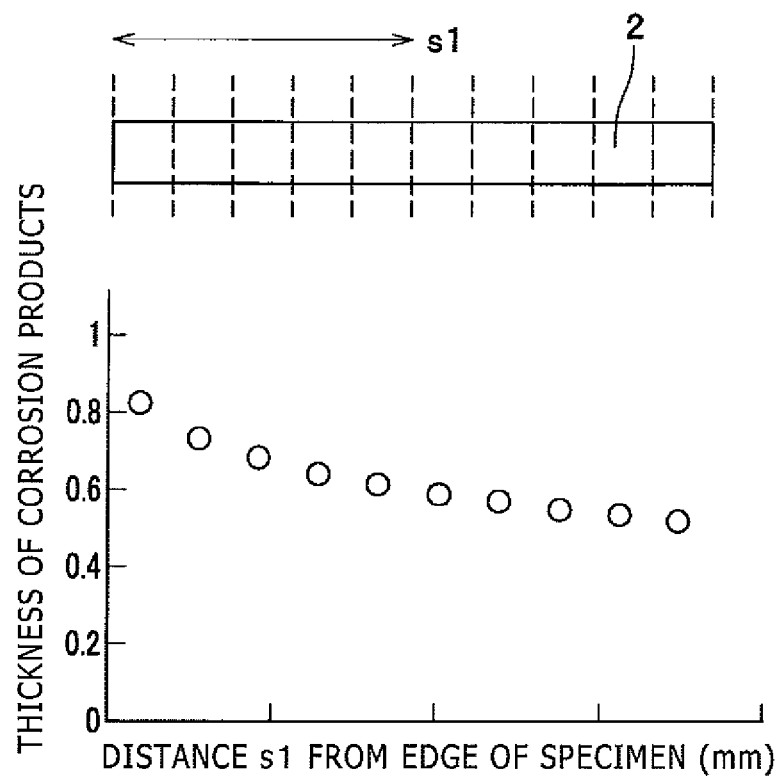
FIG. 6 is a chart showing typical measurements of the degree of corrosion along the longitudinal direction of a specimen in the corrosive environment monitoring apparatus.

FIG. 6 shows typical measurements of the degree of corrosion along the longitudinal direction of a specimen.

In the upper subfigure of FIG. 6, dashed lines over the specimen 2 are separator lines expediently indicating measurement locations. The lower subfigure in FIG. 6 is a plot showing results of measurements taken of the measurement locations separated by the dotted separator lines. In the lower graph of FIG. 6, the horizontal axis denotes the distances s1 from the upstream edge of the specimen 2, and the vertical axis represents the thicknesses of the corrosion products deposited on the surface of the specimen 2. Incidentally, the thicknesses of the corrosion products deposited on the surface of the specimen 2 are normalized (the thickness of the corrosion products on the upstream edge is taken as 1) with regard to the thickness of the corrosion products on the upstream edge of the specimen 2.

After the specimen 2 in the environment monitoring apparatus 1 is exposed to the atmosphere of the ambient environment as the measuring object for a predetermined time period, the degree of corrosion on the specimen 2 following its separation into equal intervals (dotted lines in FIG. 6) as shown in FIG. 6 is measured by gravimetric method, by quantitative analysis for corrosive gas elements using fluorescent X-rays, and by film thickness measuring through constant-current electrolysis, for example.

The farther away from the upstream edge (leftmost edge of the specimen 2 in FIG. 6) of the specimen 2, the smaller the thickness of the corrosion products on the specimen 2 becomes. That is because the corrosive substance 6 is consumed on (adheres to) the surface of the specimen 2 on the upstream side so that the volume of the corrosive substance 6 reaching the downstream side of the specimen 2 is reduced by the amount consumed. This tendency becomes more pronounced the lower the flow rate of the air flow (because the corrosive substance 6 takes more time getting consumed (adsorbed)) and the smaller the height (H, to be discussed later) from the measuring (testing) surface of the specimen 2 in the vent duct 3 (because the corrosive substance 6 has more opportunities to come into contact with the measuring (testing) surface of the specimen 2).

<Analysis of the Diffusion of the Corrosive Substance 6 in a Flowing Environment>

The diffusion of a substance (corrosive substance 6) in a flowing environment may be formulated using the convective diffusion equation (1) shown below. A description of the convective diffusion equation in connection with circular tubes is found in Corrosion Science Vol. 29, 1179-1187, 1989, "The Atmospheric Sulfidation of Silver in a Tubular Corrosion Reactor."

The convective diffusion equation is discussed below with regard to two-dimensional problems of the rectangular cross section. If it is assumed that C denotes the concentration of the corrosive substance 6; that the flowing direction of the corrosive gas is taken on the x-axis and the direction perpendicular (vertical direction) to that direction is taken on the y-axis; that D is the diffusion coefficient indicative of the rate at which the substance diffuses; that v denotes the mean flow rate inside the rectangular cross section, and that the distribution of flow rates is given as $(1-y^2/H^2)$, then the following two-dimensional convective diffusion equation holds:

$$D \cdot (\mathrm{grad}(C)) - 2 \cdot v \cdot (1-y^2/H^2) \cdot \delta C/\delta x = 0 \quad (1)$$

The following are given as boundary conditions:

$$C = Ci(x=0)$$

$$\delta C/\delta y = 0 (y=0)$$

$$-D \cdot \delta C/\delta y = Vd \cdot C(y=H/2)$$

where Ci is the concentration of the corrosive substance 6 in the ambient environment, i.e., the concentration of the corrosive substance 6 at the entrance to the vent duct 3 (at the inlet port 3$i$ shown in FIGS. 4A and 4B).

The above condition $\delta C/\delta y=0$ (y=0) indicates that the concentration gradient of the corrosive substance 6 at the center of the vent duct 3 is 0.

Vd stands for the deposition rate of the corrosive gas (corrosive substance 6) being deposited onto the surface of the specimen 2.

Part of the corrosive substance 6 colliding with the surface of the specimen 2 reacts therewith and is deposited thereon. The deposition rate Vd of the corrosive substance 6 onto the surface of the specimen 2 is expressed by the following equation (2) using a reaction probability γ (probability of the corrosive substance 6 reacting with the surface of the specimen 2 upon collision therewith):

$$VD = \gamma (Rg \cdot T/(2\pi \cdot M))^{0.5} \quad (2)$$

where Rg stands for a gas constant, T for the absolute temperature, and M for the molecular mass of the corrosive substance 6.

Figure 7:
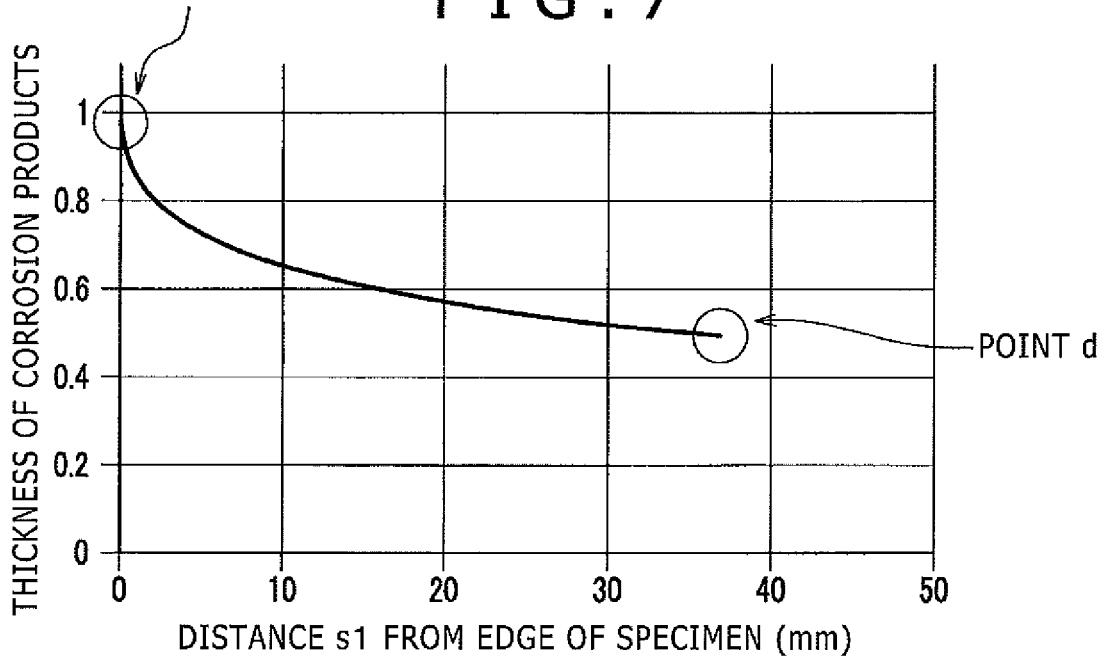
FIG. 7 is a chart showing the result of having normalized the thicknesses of corrosion products with regard to the thickness of the corrosion products on the upstream edge of a specimen in an example of analysis employing a convective diffusion equation.

FIG. 7 is a chart showing the result of having normalized the thicknesses (the thickness of the corrosion products on the upstream edge of the specimen is taken as 1) of corrosion products with regard to the thickness of the corrosion products on the upstream edge of a specimen in an example of analysis employing a convective diffusion equation.

Referring to FIG. 7, it is assumed that the specimen 2 is 47 mm long and made of silver; that the height H of the vent duct 3 above the specimen 2 (height from the measuring (testing) surface of the specimen 2) is 10 mm, and that Vd=0.01 mm/s. The thickness of the corrosion products near the downstream edge of the specimen 2 (see point d in FIG. 7) is reduced to about 50% of the thickness of the corrosion products on the upstream edge (see point c in FIG. 7).

With this embodiment, given that the thicknesses of the corrosion products in at least two locations on the specimen 2 diminish along the direction in which the corrosive gas flows or diffuses, the distribution of corrosion product thicknesses is analyzed to estimate the thickness of the corrosion products on the upstream edge of the specimen 2. Alternatively, the thickness of the corrosion products on the upstream edge of the specimen 2 is estimated by extrapolation. Since this method is not dependent on the structure of the vent duct 3 in which the specimen 2 is installed, the corrosiveness of the ambient environment as the measuring object is not underestimated.

<Another Typical Structure of the Corrosive Environment Monitoring Apparatus 1>

If the ambient environment as the measuring (testing) object is a highly corrosive environment and if the specimen 2 has been corroded to such an extent that the corrosion products thereon have peeled off, it may be impossible to evaluate accurately the thickness of the corrosion products.

Figure 8A:
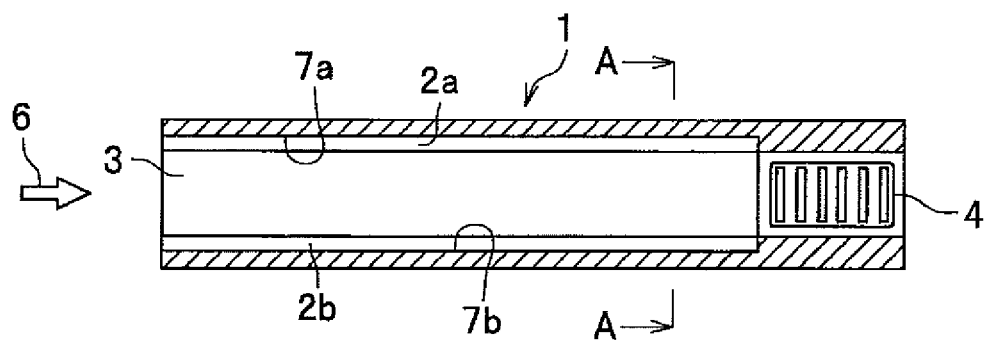
FIG. 8A is a chart showing another structure of the corrosive environment monitoring apparatus, the chart being a side view illustrating an internal structure of the corrosive environment monitoring apparatus in which specimens are attached to two planes opposed to one another in a vent duct.
Figure 8B:
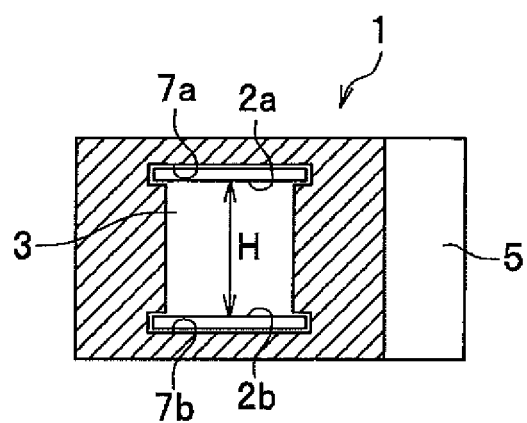
FIG. 8B is a cross-sectional view taken on line A-A in FIG. 8A.

FIGS. 8A and 8B show another structure of a corrosive environment monitoring apparatus as another embodiment. FIG. 8A is a side view illustrating an internal structure of the corrosive environment monitoring apparatus in which specimens are attached to two planes opposed to one another in a vent duct. FIG. 8B is a cross-sectional view taken on line A-A in FIG. 8A.

In this case, specimens 2$a$ and 2$b$ are attached to two planes opposite to each other of the vent duct 3 in the environment monitoring apparatus 1.

Here, grooves 7$a$ and 7$b$ are furnished around the vent duct 3, and the specimens 2$a$ and 2$b$ can be attached when inserted into the grooves 7$a$ and 7$b$.

In the above setup, the corrosive substance 6 admitted into the vent duct 3 from the ambient environment as the measuring object is diffused toward the two specimens 2$a$ and 2$b$, whereby the degree of corrosion on each of the specimens 2$a$ and 2$b$ can be reduced. In this case, narrowing (shortening) the distance (the above-mentioned size H) between the two opposed planes of the specimens 2$a$ and 2$b$ relatively lowers the amount of the corrosive substance 6 passing therebetween. This causes the flowing corrosive substance 6 to adhere relatively extensively to the specimens 2$a$ and 2$b$, whereby the effect of reducing the degree of corrosion on the specimens 2$a$ and 2$b$ is enhanced.

Figure 9A:
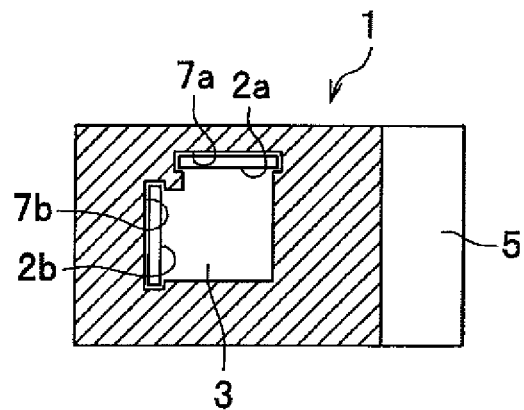
FIG. 9A is a cross-sectional view of the corrosive environment monitoring apparatus in which specimens are attached to two planes adjacent to one another in a vent duct.
Figure 9B:
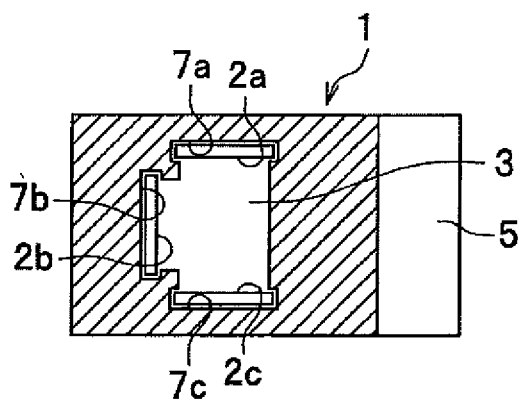
FIG. 9B is a cross-sectional view of the corrosive environment monitoring apparatus in which specimens are attached to three planes adjacent to one another in a vent duct.
Figure 9C:
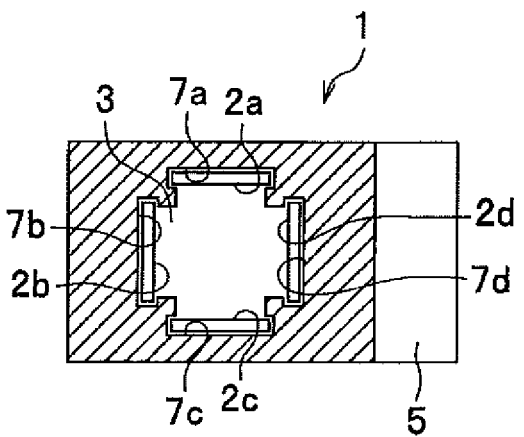
FIG. 9C is a cross-sectional view of the corrosive environment monitoring apparatus in which specimens are attached to four planes adjacent to one another in a vent duct.

FIGS. 9A, 9B and 9C are cross-sectional views of the corrosive environment monitoring apparatus in which specimens are attached to two, three, or four planes adjacent to one another in the vent duct 3. The power source 5 shown in FIGS. 9A through 9C supplies voltages to the fans 4 as mentioned above.

As shown in FIG. 9A, the specimens 2$a$ and 2$b$ may be attached to two adjacent planes forming the vent duct 3. As in the above case, the specimens 2$a$ and 2$b$ are attached as they are inserted into the grooves 7$a$ and 7$b$.

Also, depending on the intensity of corrosiveness of the environment, the specimens 2 may be attached to three or four planes forming the vent duct 3 as shown in FIGS. 9B and 9C, respectively. In the example of FIG. 9B, the specimens 2$a$, 2$b$ and 2$c$ are attached to the vent duct 3 as they are inserted into the grooves 7$a$, 7$b$ and 7$c$ furnished around the vent duct 3. Likewise, in the example FIG. 9C, the specimens 2$a$, 2$b$, 2$c$ and 2$d$ are attached to the vent duct 3 as they are inserted into the grooves 7$a$, 7$b$, 7$c$ and 7$d$ furnished around the vent duct 3.

Figure 10A:
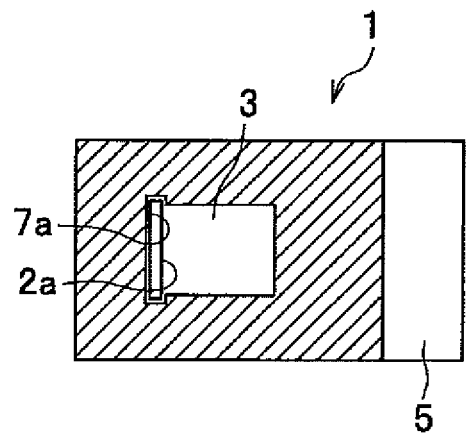
FIG. 10A is a cross-sectional view of the corrosive environment monitoring apparatus in which a specimen is attached perpendicularly to one plane.
Figure 10B:
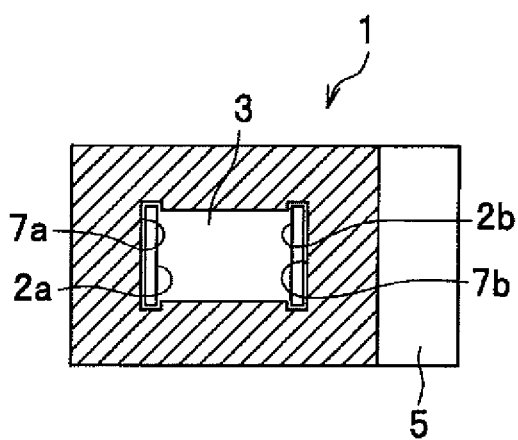
FIG. 10B is a cross-sectional view of the corrosive environment monitoring apparatus in which specimens are attached perpendicularly to two planes opposed to one another.
Figure 11A:
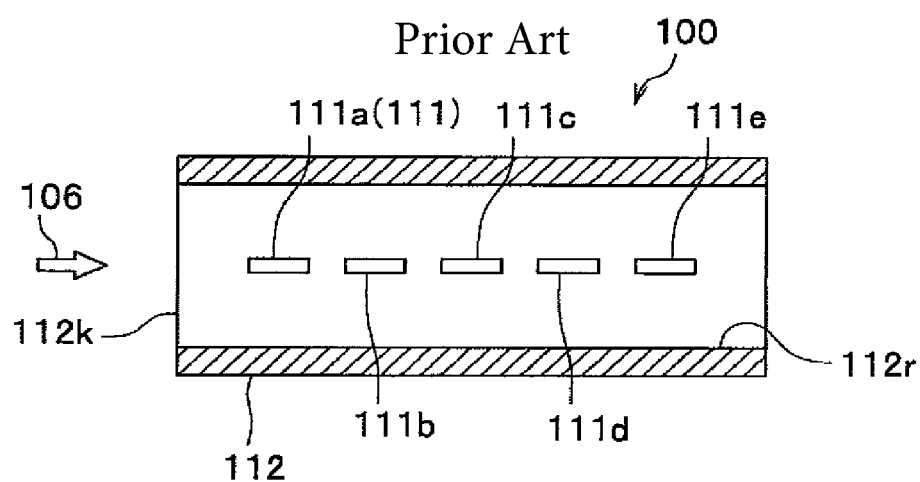
FIG. 11A is a side view showing an internal structure of a protective case of a typical prior art environment monitoring apparatus.
Figure 11B:
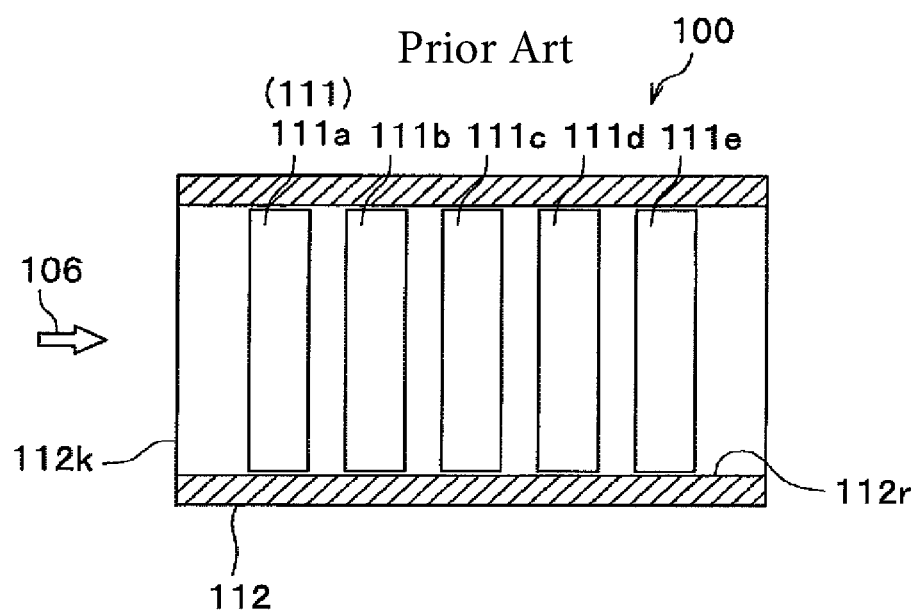
FIG. 11B is a top view showing the internal structure of the protective case of the typical prior art environment monitoring apparatus.
Figure 12:
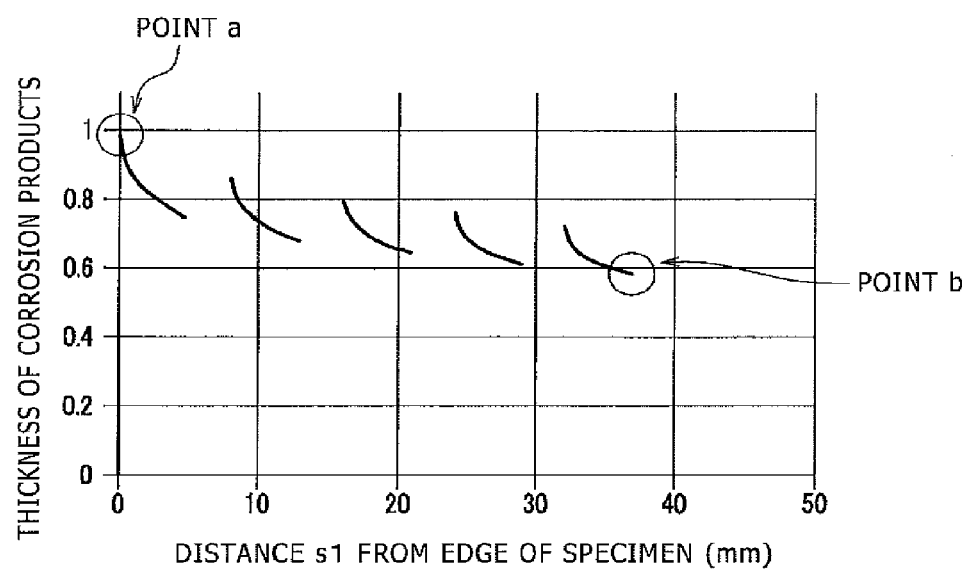
FIG. 12 is a chart showing the result of having normalized the thicknesses of corrosion products with regard to the thickness of the corrosion products on the upstream edge of prior art specimens using a convective diffusion equation.
Figure 13:
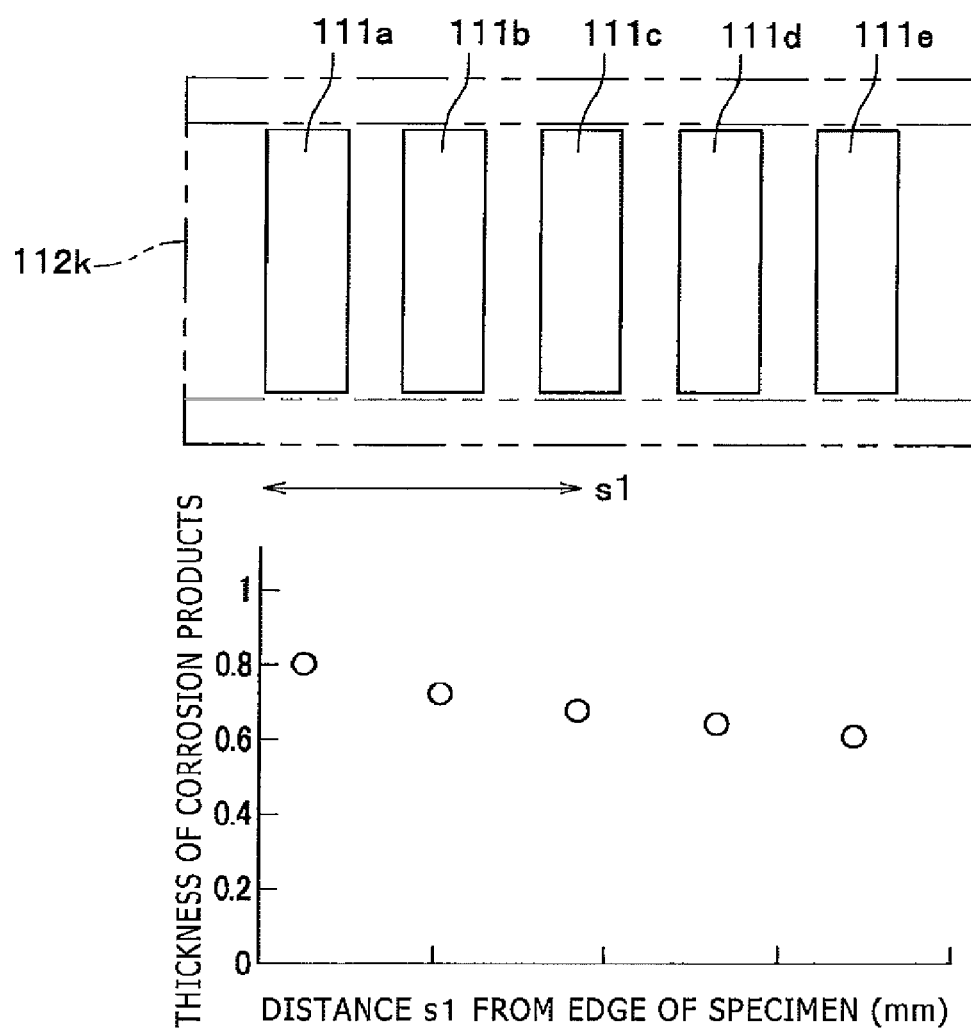
FIG. 13 is a chart showing typical measurements of the degree of corrosion on specimens exposed to the target ambient environment for a predetermined time period using a prior art environment monitoring apparatus.

FIGS. 10A and 10B are cross-sectional views of another typical corrosive environment monitoring apparatus in which a specimen is attached perpendicularly to one plane or two planes in a vent duct.

If those surfaces (exposed surfaces) of the specimens 2 (2$a$, 2$b$) subject to measurement are arranged perpendicularly as shown in FIGS. 10A and 10B, the arrangement is all the more preferable because evaluation can be performed in such a manner that the effect of gravity on the corrosive substance present in the ambient environment being measured (tested) is suppressed as much as possible.

Also, if a notch or an opening into which the specimen 2 is inserted is formed on the front side of the groove 7 of the vent duct 3 in the corrosive environment monitoring apparatus 1, the formation is all the more preferable because that makes it easier to install and collect (mount and dismount) the specimen 2. This formation can be applied to all the structures explained above.

The above-described structures permit measurement of the degree of corrosion on the specimens 2 that were left for a predetermined time period in the ambient (installation) environment as the measuring object before being collected. The structures thus make it possible to evaluate the corrosiveness of the installation environment for electrical and electronic equipment simply and accurately in a short time period. The evaluations provide the basis for allowing the corrosion prevention measures corresponding to the degree of corrosiveness of the environment to be reflected in the design and maintenance of the equipment.

It is therefore possible to implement a corrosive environment monitoring apparatus and a corrosive environment monitoring method for evaluating the corrosiveness of the installation environment for electrical and electronic equipment simply and accurately in a short time period.

<<Other Embodiments>>

Although the embodiments above were shown to use the specimens 2 made entirely of metallic materials for example, each specimen 2 needs only be made of a metallic material at least in a part where corrosion products are to be formed (i.e., in regions subject to measurement of the corrosive characteristics of the ambient environment). There is no need for the entire specimen 2 to be made of a metallic material.

For example, a metal may be mounted on a plastic base (substrate). In this case, costs can be lowered because only part of each specimen is metallic.

The metal layer may be formed by selectively resorting to plating, sputtering, vapor deposition, or some other suitable technique.

On balance, the corrosiveness explained in conjunction with the embodiments above may apply rather to light electrical appliances than to heavy electrical appliances because the former tend to have wiring patterns and connecting terminals that are finely structured. Still, the present invention can be applied extensively to any ambient (installation) environment where corrosiveness constitutes a problem for the light and heavy electrical appliances as well as for other facilities.

DESCRIPTION OF REFERENCE CHARACTERS

1 Corrosive environment monitoring apparatus
2, 2a, 2b, 2c, 2d Specimen
3, 3a, 3b, 3c Vent duct
4 Fan (feeding means)
5 Power source
6 Corrosive substance

The invention claimed is:

1. A corrosive environment monitoring apparatus comprising:
at least two vent ducts, each vent duct having at least one specimen installed therein, the corrosive environment monitoring apparatus adapted to measure the corrosiveness in an ambient environment from the corroded condition of at least one specimen;
wherein each specimen has a region subject to the measurement, the region being made of a metallic material; and
wherein the vent ducts are arranged in parallel with one another.

2. The corrosive environment monitoring apparatus according to claim 1, further comprising feeding means which feeds a corrosive substance in the ambient environment to the region subject to the specimen measurement placed in each vent duct.

3. The corrosive environment monitoring apparatus according to claim 2 wherein the feeding means is a fan located downstream of the flow of the corrosive substance around the specimen in each vent duct.

4. The corrosive environment monitoring apparatus according to claim 1, wherein the metallic material is copper or silver.

5. The corrosive environment monitoring apparatus according to claim 1, wherein the region subject to the specimen measurement is configured to be measured for the degree of corrosion in at least two locations along the direction in which the corrosive substance flows, so that the corrosiveness in the ambient environment is acquired based on how the measured degrees of corrosion are distributed.

6. The corrosive environment monitoring apparatus according to claim 1, wherein there are a plurality of the specimens in each vent duct, and
wherein the regions subject to the specimen measurement are arranged opposite or adjacent to one another.

7. The corrosive environment monitoring apparatus according to claim 1, wherein the region subject to the specimen measurement has planes exposed to the ambient environment, the planes being arranged perpendicularly.

8. The corrosive environment monitoring apparatus according to claim 1, wherein the metal substance of each specimen in each vent is the same metal substance and is different from the metal substance of each specimen in each other vent.

9. A corrosive environment monitoring method, comprising:
providing at least two vent ducts, each vent duct having at least one specimen installed therein;
measuring the corrosiveness in an ambient environment from the corroded condition of at least one specimen;
wherein each specimen has a region subject to the measurement, the region being made of a metallic material; and
wherein the vent ducts are arranged in parallel with one another.

10. The corrosive environment monitoring method according to claim 9, wherein a corrosive substance in the ambient environment is forcibly fed to the region subject to the specimen measurement formed in each vent duct.

11. The corrosive environment monitoring method according to claim 10, wherein the corrosive substance in the ambient environment is sucked from downstream of the flow of the corrosive substance around the specimen and is fed to the region subject to the specimen measurement.

12. The corrosive environment monitoring method according to claim 9, wherein the metallic material is copper or silver.

13. The corrosive environment monitoring method according to claim 9, wherein the region subject to the specimen measurement is measured for the degree of corrosion in at least two locations along the direction in which the corrosive substance flows, so that the corrosiveness of the ambient environment is acquired based on how the measured degrees of corrosion are distributed.

14. The corrosive environment monitoring method according to claim 9, wherein there are a plurality of the specimens in each vent duct, and
   wherein the regions subject to the specimen measurement are arranged opposite or adjacent to one another for monitoring.

15. The corrosive environment monitoring method according to claim 9, wherein the region subject to the specimen measurement has planes exposed to the ambient environment, the planes being arranged perpendicularly for monitoring.

16. The corrosive environment monitoring method according to claim 9, wherein the metal substance of each specimen in each vent is the same metal substance and is different from the metal substance of each specimen in each other vent.

* * * * *